United States Patent
Liu et al.

(10) Patent No.: US 11,779,041 B2
(45) Date of Patent: Oct. 10, 2023

(54) PLANT EXTRACTION METHOD

(71) Applicants: BEIJING WEHAND-BIO PHARMACEUTICAL CO., LTD, Beijing (CN); GUANGXI WEHAND-BIO PHARMACEUTICAL CO., LTD, Guangxi (CN)

(72) Inventors: Yuling Liu, Beijing (CN); Xiangyang Zhu, Beijing (CN); Yiqun Jin, Beijing (CN); Zhihua Liu, Beijing (CN); Jundong Yang, Beijing (CN)

(73) Assignees: BEIJING WEHAND-BIO PHARMACEUTICAL CO., LTD, Beijing (CN); GUANGXI WEHAND-BIO PHARMACEUTICAL CO., LTD, Hechi (CN)

( * ) Notice: Subject to any disclaimer, the term of this patent is extended or adjusted under 35 U.S.C. 154(b) by 0 days.

(21) Appl. No.: 17/638,011

(22) PCT Filed: Aug. 20, 2020

(86) PCT No.: PCT/CN2020/110179
§ 371 (c)(1),
(2) Date: Feb. 24, 2022

(87) PCT Pub. No.: WO2021/036896
PCT Pub. Date: Mar. 4, 2021

(65) Prior Publication Data
US 2022/0273014 A1    Sep. 1, 2022

(30) Foreign Application Priority Data
Aug. 27, 2019 (CN) .......................... 201910794907.2

(51) Int. Cl.
| | |
|---|---|
| A61K 36/60 | (2006.01) |
| A23L 33/105 | (2016.01) |
| A61P 3/06 | (2006.01) |
| A61P 3/10 | (2006.01) |
| A61P 1/00 | (2006.01) |
| A61K 36/34 | (2006.01) |
| A61K 36/896 | (2006.01) |

(52) U.S. Cl.
CPC ............ *A23L 33/105* (2016.08); *A61K 36/34* (2013.01); *A61K 36/60* (2013.01); *A61K 36/896* (2013.01); *A61P 1/00* (2018.01); *A61P 3/06* (2018.01); *A61P 3/10* (2018.01); *A61K 2236/51* (2013.01); *A61K 2236/55* (2013.01)

(58) Field of Classification Search
None
See application file for complete search history.

(56) References Cited

U.S. PATENT DOCUMENTS

| | | |
|---|---|---|
| 9,066,960 B2 | 6/2015 | Liu et al. |
| 2015/0224160 A1 | 8/2015 | Xie et al. |
| 2022/0273014 A1 | 9/2022 | Liu et al. |

FOREIGN PATENT DOCUMENTS

| | | | | |
|---|---|---|---|---|
| CN | 1611487 A | 5/2005 | | |
| CN | 1850166 A | 10/2006 | | |
| CN | 1313435 C | 5/2007 | | |
| CN | 1981814 A | 6/2007 | | |
| CN | 100464764 C | 3/2009 | | |
| CN | 102462817 A | 5/2012 | | |
| CN | 104402801 A | 3/2015 | | |
| CN | 104557675 A | * 4/2015 | ........... | C07D 211/46 |
| CN | 104844723 A | 8/2015 | | |
| CN | 107362200 A | * 11/2017 | ........... | A61K 36/605 |
| CN | 107362200 A | 11/2017 | | |
| CN | 110393738 A | 11/2019 | | |
| CN | 2021/036896 A1 | 3/2021 | | |
| EP | 4 023 239 A1 | 7/2022 | | |
| JP | 2010-536804 A | 12/2010 | | |
| JP | 2013-504607 A | 2/2013 | | |
| JP | 2022-544422 A | 10/2022 | | |

OTHER PUBLICATIONS

Christenhusz (Phytotaxa (2016), vol. 261, No. 3, pp. 201-217).*
Deng (Animal Husbandry and Feed Science (2016), vol. 8, No. 4, pp. 230-233).*
Nov. 16, 2020 International Search Report issued in International Patent Application No. PCT/CN2020/110179.
Xia, Xuejun et al. "Determination of Mulberry Twig Alkaloids By RP-HPLC with Pre Column Derivatization", Chinese Journal of New Drugs, (2008), vol. 17, No. 23, pp. 2044-2047.
Shen, Aiying et al., "Studies on the Extraction Technology of Water-soluble Polysaccharides From Mulberry Leaf", China Academic Journal Electronic Publishing House, (2004), vol. 30, No. 3, pp. 277-279.

(Continued)

*Primary Examiner* — Susan Hoffman
(74) *Attorney, Agent, or Firm* — Oliff PLC (57) ABSTRACT

A plant extraction method includes the following steps: 1) preparation of a crude plant extraction solution; 2) separation of the crude extraction solution through a cation resin and an optional anion resin to obtain a collection solution; 3) concentration of the collection solution obtained in step 2); 4) alcohol precipitation of the concentration solution obtained in step 3); and optionally, step 5) concentration and drying. The method can effectively reduce the content of heavy metals in an extract, and reduce the amount of ethanol used in extraction, thereby improving the product quality and lowering the production cost, and the efficiency and safety of industrial production are improved. The extract obtained by this method can be used to prepare drugs for lowering blood lipid, treating abnormal glucose tolerance, treating diseases related to abnormal blood glucose, or regulating intestinal flora, and can be processed into food products, health-care products or drinks.

15 Claims, 1 Drawing Sheet

(56) References Cited

OTHER PUBLICATIONS

Chang, Xing-jie et al., "Study on Forsythiaside-A and Forsythin and Antibacterial Activity Change in Preparation Process of Water Decoction and Alcohol Precipitation of Lianqiao (Forsythia Suspensa Vahl)", Guiding Journal of Traditional Chinese Medicine and Pharmacy, (May 2018), vol. 24, No. 9, pp. 39-41.

Zhai, Wenjun et al., "Research on the Divided Extraction of Rodgersia Aesculifolia-Batal and the Compound Formation," Journal of Shaanxi Institute of Education, vol. 12, No. 1, pp. 77-80, Mar. 31, 1996.

Wang, X. et al., "Non-official translation: Pharmacological Study of Erycibe obtusifolia Benth Causing Pupil Constriction," Journal of New Medicine, vol. 9, No. 6, pp. 279-280, Jun. 1, 1978.

Ling, L. et al., "Study on production technoligy of steviosin extraction from Stevia rebaudiana," Science and Technology of Food Industry, vol. 34, No. 6, pp. 257-261, Mar. 15, 2013.

\* cited by examiner

PLANT EXTRACTION METHOD

TECHNICAL FIELD

The present disclosure belongs to the technical field of plant extraction, specifically relates to a plant extraction method.

BACKGROUND

Natural plant extracts refer to products obtained by using plants as raw materials and specifically obtaining or concentrating one or more active components in plants without changing the active structure thereof via physical and chemical extraction and separation according to the use of the final extracted product. Plant extracts contain rich and complex organic components, wherein the majority of the organic components have biological activities such as antibacterial activity, bacteriostatic activity, antioxidative activity and the activity of regulating the immunity of body. Being environmentally friendly, healthy, safe, efficient, and residue-free, etc., plant extracts are widely used in fields such as medicines, health care products, cosmetics, food additives, pesticides, feed and daily necessities all over the world. China is the cradle of silkworm industry. Plants of Moraceae have been considered as precious materials used as medicine and food since ancient times due to their high nutritional value and medicinal value, which is recorded in traditional Chinese medicine classics in all ages, for example, as early as in the Compendium of *Materia medica*, there are descriptions of "the decoction of the mulberry leaf juice can quench thirst in place of tea" and "drinking after being cooked and decocted can quench thirst in place of tea". Modern science has also proved the nutritional components and the pharmacologically active components of the plants of Moraceae as well as the mechanisms of action thereof. Researches have indicated that the chemical components in the plants of Moraceae mainly include flavone compounds, polysaccharide compounds, alkaloids and amino acids, in addition to some volatile oils, tannin, succinic acid, adenine, vitamins, and the like, and have antifungal effect, anti-inflammatory effect, hypoglycemic effect, antioxidative effect, and the like.

Plant extraction methods may be classified into classical extraction methods and modern extraction methods. Classical extraction methods do not require special instruments, are simple and easy to operate, have low extraction cost, and mainly include solvent extraction method, steam distillation method, and the like. Modern extraction methods are extraction methods based on modern advanced instruments or newly developed extraction methods, and mainly include ultrasonic extraction method, microwave extraction method, enzyme extraction method, solid phase extraction method, and the like. The components of plant extracts may be classified into lipophilic components and hydrophilic components, which may be obtained by selecting different solvents and/or extraction methods for different plant extracts. For example, as for lipophilic plant components, organic solvents may be used to conduct percolation, cold leaching, ultrasonic extraction, microwave extraction, reflux extraction, and the like; as for water-soluble components, a commonly used extraction method is water extraction and alcohol precipitation method, which is of great significance in terms of the refining and purification, the increase of the content of active components, the decrease of dosage of administration and the convenience in production and molding of the extracts of traditional Chinese medicine. The specific steps include steps such as water extraction, concentration, alcohol precipitation, drying, and the like, wherein alcohol precipitation refers to adding ethanol to the crude extraction solution until the concentration of ethanol reaches an appropriate concentration to allow impurities insoluble in ethanol to precipitate, and then conducting solid-liquid separation to achieve the purpose of refining. For example, Xingjie Chang, et al. extracted the active components of Forsythia in accordance with the steps of decoction with water, concentration, ethanol precipitation and recovery of ethanol (Xingjie Chang, Qian Ding. Forsythiaside A, Forsythin and changes of the bacteriostatic activities thereof in the preparation process of water extraction and alcohol precipitation of Forsythia [J]. Guiding Journal of Traditional Chinese Medicine and Pharmacy, 2018, 24(9):39-41); Aiying Shen, et al. obtained mulberry leaf polysaccharides by using water extraction and ethanol precipitation method (Aiying Shen, Ziyu Zhu, Wenliang Zhang. Study on the extraction process of water-soluble polysaccharides from mulberry leaves [J]. Acta Sericologica Sinica, 2004, 30(3):277-279). In order to further concentrate and enrich the active components, resin separation, membrane separation, ultrafiltration, dialysis and the like may also be conducted after alcohol precipitation, so as to achieve the purpose of purification.

The increasing demand of consumers for plant extract products has prompted great development of plant extraction process, and the quality of the products has been improved. However, compared with developed countries, there are still some prominent problems in Chinese plant extracts. Among these, product safety issues such as the residue of heavy metals and pesticides have attracted extensive attention. It has been found by researches that some plants are capable of enriching the heavy metals (such as copper, lead, cadmium, zinc, etc.) in the environment. For example, the research conducted by Xing Zhang, et al. shows that, in a case where a mulberry is grown on soil containing the following heavy metals, i.e., Cu (593.56 mg/kg), Pb (825.41 mg/kg), Cd (8.11 mg/kg), Zn (705.41 mg/kg), the contents of heavy metals measured in roots are up to the following contents, i.e., Cu: 33.13 mg/kg, Pb: 33.13 mg/kg, Cd: 4.53 mg/kg, Zn: 317.72 mg/kg, the contents of heavy metals in leaves are up to the following contents, i.e., Cu: 13.18 mg/kg, Pb: 10.32 mg/kg, Cd: 1.90 mg/kg, Zn: 186.53 mg/kg, which far exceeds the relevant regulations (according to the regulations of "*Green Trade Standards of Medicinal Plants and Preparations for Importing and Exporting*", in the raw materials, decoction pieces, extracts and preparations of plants, the total content of heavy metals is 20.0 mg/kg or less, the concent of Pb is 5 mg/kg or less, the content of Cd is 0.3 mg/kg or less, the content of Hg is 0.2 mg/kg or less, the content of Cu is 20.0 mg/kg or less, and the content of As is 2.0 mg/kg or less). How to reduce the residues of harmful substances such as heavy metals to the greatest extent is an important aspect required to be considered in the research of plant extraction methods.

SUMMARY

In general researches and industrial production processes, water-soluble plant extracts are generally obtained by water extraction and alcohol precipitation method, and resin separation, membrane separation, ultrafiltration, dialysis and the like would be conducted after alcohol precipitation for further enrichment and purification when considering increasing the content of a specific component. However, as for plant extracts, especially plants like plants of Moraceae that are prone to enrich the heavy metals in the environment, using such extraction method to obtain extracts is not sufficient to remove the heavy metal residues in the extracts. It has been found by the present inventors based on repeated research that, during the extraction process of the plant, subjecting the crude extraction solution to resin separation, concentration and alcohol precipitation successively is not only capable of improving the separation efficiency of the active components, but also capable of reducing the heavy metal residues in the plant extracts significantly. Based on such finding, the present inventors provide a novel plant extraction method, which is capable of effectively reducing the content of the heavy metals in the plant extracts while greatly reducing the amount of ethanol used in the extraction process, thereby improving the quality of the product while reducing the production cost, and improving the efficiency and safety of industrial production to a certain extent.

In view of this, in the first aspect, the present disclosure provides a plant extraction method comprising the following steps of:

step 1): preparing a crude plant extraction solution;

step 2): separating the crude extraction solution via a cation resin to collect the eluate, optionally, separating the eluate via an anion resin to collect the effluent;

step 3): concentrating the collection solution obtained in step 2);

step 4): subjecting the concentrated solution obtained in step 3) to alcohol precipitation;

and optionally, step 5): concentrating and drying.

1) Preparing the Crude Plant Extraction Solution

In the present disclosure, the plant is preferably a plant of Moraceae, Liliaceae, Campanulaceae, or Commelinaceae, further preferably a plant of *Morus, Hyacinthus, Adenophora*, or *Commelina*, and more preferably, the plant is any one or a combination of more selected from *Morus multicaulis* Perrott., *Morus alba* L., *Morus atropurpurea* Roxb, *Morusmizuho* Hotta, *Morus wittiorum* Hand Mazz., *Morus laevigata* Wall, *Morus nigra* Linn., *Morus cathayana* Hemsi., *Morus serrata* Roxb., *Morus mongolica* Schneid., *Morus bombycis* Koidz., *Morus notabilis* Schneid., *Morus nigriformis* Koidz., *Morusyunnanensis* Koidz., *Morus australis* Poir., *Morus mongolica* (Bur.) Schneid var. diabolica Koidz., *Morus alba* L. var. *macrophylla* loud, *Morus alba* Var. *Pendula* Dippel, *Morus alba* L. var. *venosa* Delili, a mulberry variety bred from the above mulberry species, a hybrid mulberry obtained from selective intra-species or inter-species breeding of the above mulberry species, *Hyacinthus orientalis, Adenophora. triphylla* var. *japonica*, and *Commelina communi*; preferably, the plant is *Morus atropurpurea* Roxb, *Morus multicaulis* Perrott., *Morus alba* L., *Morus serrata* Roxb., *Morus bombycis* Koidz., or a hybrid mulberry, the hybrid mulberry is preferably Yuesang No. 11, Guisangyou No. 62 or Sangteyou No. 2. Various parts such as the leaf, root, branch, bark, bud, stem, and fruit of the plant may be used.

The plant may be subjected to crude extraction with a solvent such as alcohol-water, water, an alkaline aqueous solution or an acidic aqueous solution, preferably, the solvent used for the crude extraction is water.

During extraction, it is preferred to crush the plant and then add the resultant into water to conduct heat extraction, the extraction duration is preferably 0.5 h to 3$h$ for each extraction, and the extraction is conducted 1 to 3 times.

In a preferred embodiment, the crushed plant may be added into an extraction tank to conduct extraction.

During extraction, the more the addition amount of the solvent, the higher the extraction rate of the plant. However, the addition amount of the solvent being excessive may increase the difficulty of subsequent separation and purification. The addition amount of the solvent is preferably 3 to 20 times and more preferably 4 to 15 times the weight of the charged plant raw material, which is capable of obtaining the plant extract to the greatest extent without excessively increasing the volume of the solution and increasing the difficulty of subsequent processing.

Extraction may be conducted by using decocting method, ultrasonic extraction method or reflux extraction method, preferably conducted by using decocting method or reflux extraction method, and more preferably conducted by using decocting method which has more mature industrial equipment.

Optionally, extraction may be conducted repeatedly and the extracting solutions are combined.

Preferably, the extracting solution is filtered to remove insoluble matters, so as to obtain the crude plant extraction solution.

2) Separation Via Cation Resin and Optional Anion Resin

In the present disclosure, the components in the crude plant extraction solution are separated by using ion exchange resin.

In step 2), the crude plant extraction solution is loaded onto the cation resin and separated via the cation resin. Preferably, after being packed into the column, the cation resin is subjected to activation by being washed with an acidic solution, an alkaline solution and an acidic solution successively. The activation method of the resin is also capable of realizing the adjustment of the pH value of the resin environment, thereby optimizing the adsorption selectivity of the cation resin and enhancing the separating effect.

Preferably, the resin is washed with an alkaline solution until the pH of the eluate is 8.0 to 9.5, preferably 8.5 to 9.5.

Preferably, the alkaline solution is ammonia solution, sodium hydroxide solution, potassium hydroxide solution or sodium carbonate solution, preferably ammonia solution or sodium hydroxide solution. Preferably, the concentration of the alkaline solution is 0.5 to 4 mol/L, preferably 1 to 2 mol/L.

Preferably, the resin is washed with an acidic solution until the pH of the eluate is 3.0 to 7.0, preferably 4.5 to 6.5.

Preferably, the acidic solution is selected from hydrochloric acid solution, phosphoric acid solution and disodium hydrogen phosphate-citric acid buffer, and is more preferably disodium hydrogen phosphate-citric acid buffer. Preferably, the concentration of the acidic solution is 0.5 to 4 mol/L, preferably 1 to 2 mol/L.

When disodium hydrogen phosphate-citric acid buffer is used as the acidic solution, the pH value of the disodium hydrogen phosphate-citric acid buffer is preferably 4.0 to 6.5, and more preferably 4.5 to 5.0.

Optionally, the cation resin may also be washed with deionized water having a volume of 3 to 5 times the column volume after the last washing with the acidic solution.

Preferably, the cation resin is one or a combination of more selected from a strongly acidic cation exchange resin, a weakly acidic cation exchange resin and a strongly alkaline quaternary ammonium-type cation resin.

Preferably, the cation resin is one or a combination of more selected from 732-type strongly acidic styrene-based cation exchange resin, 734-type strongly acidic styrene-based cation exchange resin, 002SC-type strongly acidic styrene-based cation exchange resin, D001-type macroporous and strongly acidic styrene-based cation exchange resin, D113-type macroporous and weakly acidic phenylpropene-based cation exchange resin and D254-type macroporous and strongly alkaline quaternary ammonium-type cation exchange resin.

Preferably, the cation resin is 732-type strongly acidic styrene-based cation exchange resin, 734-type strongly acidic styrene-based cation exchange resin and D001-type macroporous and strongly acidic styrene-based cation exchange resin.

It has been found by the research that, without being bound by any theory, the loading process of the cation exchange resin, especially the concentration of the loading solution and the amount of resin used, has significant influence on the adsorption and separation effects of plant components.

Preferably, the amount of the cation resin used and the charged plant raw material has a weight ratio ranging from 1:1 to 1:30, preferably 1:1 to 1:25, and more preferably 1:2 to 1:20.

After loading the crude plant extraction solution onto the cation resin, the loaded cation resin is subjected to elution with an eluent. Preferably, the eluent is a salt solution or an alkaline solution containing cations, preferably one or more selected from sodium chloride, ammonium chloride, ammonium sulfate, ammonium nitrate, ammonia water, potassium chloride and sodium hydroxide.

Preferably, the cations in the eluent have a concentration ranging from 0.04 to 5 mol/L, preferably 0.2 to 3 mol/L, and more preferably 0.5 to 2.5 mol/L.

Preferably, the flow rate of the eluent is 1 to 15 BV/h, preferably 5 to 10 BV/h.

Preferably, the weight of the eluent used for the separation via cation resin is 0.1 to 30 times the weight of the charged plant raw material. Preferably, the elution is conducted with the eluent, of which the weight is 0.5 to 10 times the weight of the charged plant raw material.

Collection begins when the eluate flows out of the cation resin. The starting point of the collection may be determined according to the pH of the effluent obtained from the cation resin, for example, when an alkaline solution such as ammonia water is used for conducting elution, collection begins when the pH of the effluent obtained from the cation resin is higher than 7. The starting point of the collection may also be determined according to the properties of the components to be separated, for example, the starting point of the collection of the effluent may be determined by utilizing a chromogenic reaction or a precipitation reaction. Also, the starting point of the collection may be determined by using detection methods such as high performance liquid chromatography. Preferably, the collection is terminated when the volume of the collection solution reaches 0.1 to 10 times the weight of the charged plant raw material, and more preferably, the collection is terminated when the volume of the collection solution reaches 0.2 to 5 times the weight of the charged plant raw material.

During the separation via the cation resin, fixed-bed ion exchange process may be adopted, and continuous ion exchange process may also be adopted. Preferably, continuous ion exchange process with higher degree of automation is used.

In order to improve the separation effect of the cation resin, it is also possible to conduct multiple separations via the cation resin, for example, 2 to 5 times of separation.

Optionally, the collected eluate is separated via an anion resin. Upon separation via the anion resin, the anion resin is subjected to activation by being washed with an alkaline solution, an acidic solution and an alkaline solution successively after being packed into the column.

Preferably, the anion resin is washed with an acidic solution until the pH of the eluate is 3.0 to 7.0, preferably 4.5 to 6.5.

Preferably, the acidic solution is selected from hydrochloric acid solution, phosphoric acid solution, and disodium hydrogen phosphate-citric acid buffer, and more preferably disodium hydrogen phosphate-citric acid buffer. Preferably, the concentration of the acidic solution is 0.5 to 4 mol/L, preferably 1 to 2 mol/L. When disodium hydrogen phosphate-citric acid buffer is used as the acidic solution, the pH value of the disodium hydrogen phosphate-citric acid buffer is preferably 4.0 to 6.5, and more preferably 4.5 to 5.0.

Preferably, the anion resin is washed with an alkaline solution until the pH of the eluate is 8.0 to 9.5, preferably 8.5 to 9.5.

Preferably, the alkaline solution is ammonia solution, sodium hydroxide solution, potassium hydroxide solution or sodium carbonate solution, preferably sodium hydroxide solution. Preferably, the concentration of the sodium hydroxide solution is 0.5 to 4 mol/L, preferably 1 to 2 mol/L.

Preferably, the anion resin is one or a combination of more selected from a strongly alkaline anion exchange resin, a weakly alkaline anion exchange resin and a weakly acidic anion exchange resin.

Preferably, the anion resin is one or a combination of more selected from 717-type strongly alkaline styrene-based anion exchange resin, 711-type strongly alkaline styrene-based anion exchange resin, D201-type macroporous and strongly alkaline styrene-based anion exchange resin, D218-type macroporous and strongly alkaline acrylic-based anion exchange resin, D301-G-type macroporous and weakly acidic styrene-based anion exchange resin and D301-type macroporous and weakly alkaline styrene-based anion exchange resin.

Preferably, the anion resin is 717-type strongly alkaline styrene-based anion exchange resin, D201-type macroporous and strongly alkaline styrene-based anion exchange resin, and D218-type macroporous and strongly alkaline acrylic-based anion exchange resin.

Preferably, the amount of the anion resin used and the charged plant raw material has a weight ratio ranging from 1:1 to 1:80, preferably 1:1 to 1:64, and more preferably 1:1 to 1:32.

Collection begins when the liquid flows out of the anion resin. Preferably, the collection is terminated when the volume of the collection solution reaches 0.05 to 10 times the weight of the charged plant raw material, and more preferably, the collection is terminated when the volume of the collection solution reaches 0.1 to 5 times the weight of the charged plant raw material.

Optionally, in order to improve the separation effect of the anion resin, it is also possible to conduct multiple separations via the anion resin, for example, 2 to 4 times of separation.

Preferably, the extraction method further comprises a step of concentrating the crude plant extraction solution prior to the separation in step 2).

Methods for concentrating the crude extraction solution include concentration by heating, concentration by nanofiltration membrane, concentration by reverse osmosis membrane and the combination thereof.

Concentration is preferably conducted via concentration by heating, concentration by reverse osmosis membrane, or the combination thereof, so as to increase the concentration of the crude plant extraction solution.

Preferably, when using a reverse osmosis membrane and a nanofiltration membrane to conduct concentration, in order to improve the efficiency of the concentration, purities may be removed by conducting centrifugation, filtration via ultrafiltration membrane or filtration via microfiltration membrane prior to the concentration via reverse osmosis membrane and nanofiltration membrane.

Preferably, the crude plant extraction solution is concentrated until the mass concentration of the solid content in the solution is 1% to 15%, preferably 2% to 10%. The solid content refers to the solid substance remained after the water in the solution is removed.

Optionally, the concentrated crude extraction solution may also be subjected to alcohol precipitation prior to the resin separation in step 2). During the alcohol precipitation, ethanol is added to the crude extraction solution, the mixture is stirred and mixed evenly, the stirring is stopped, and the resultant is allowed to stand for a certain period of time to precipitate the insoluble matters therein. Preferably, ethanol is added to the crude plant extraction solution, in which the volume of ethanol is 0.2 to 20 times the volume of the crude plant extraction solution, preferably 0.4 to 10 times the volume of the crude plant extraction solution. More preferably, alcohol precipitation is conducted by using an alcohol precipitation tank. Preferably, the stirring speed in alcohol precipitation is 10 to 600 rpm, preferably 40 to 500 rpm, and more preferably 80 to 400 rpm.

3) Concentrating the Collection Solution Obtained in Step 2)

The methods for concentration treatment in step 3) include concentration by heating, concentration by nanofiltration membrane, concentration by reverse osmosis membrane and the combination thereof. Preferably, purities may be removed by conducting centrifugation, filtration via ultrafiltration membrane or filtration via microfiltration membrane prior to the concentration via reverse osmosis membrane and nanofiltration membrane.

Preferably, the specific gravity of the concentrated liquid obtained in step 3) is 1.0 to 1.3. The specific gravity refers to the mass ratio of the concentrated liquid to water under the conditions that the concentrated liquid and the water have the same volume.

4) Alcohol Precipitation

In the alcohol precipitation in step 4), the concentrated solution of step 3) is subjected to treatment with ethanol. Specifically, ethanol is added to the concentrated solution of step 3), the mixture is stirred and mixed evenly, the stirring is stopped, and the resultant is allowed to stand for a certain period of time to precipitate the insoluble matters therein.

Preferably, in step 4), the ethanol used for alcohol precipitation and the charged plant raw material has a weight ratio ranging from 1:4 to 1:600, preferably 1:20 to 1:300.

Alcohol precipitation is preferably conducted in alcohol precipitation tank.

Preferably, in the alcohol precipitation in step 4), the stirring speed is 10 to 600 rpm, preferably 40 to 500 rpm, and more preferably 80 to 400 rpm.

5) Concentrating and Drying

Optionally, the extraction method further comprises step 5) of concentrating and drying.

The solution that has been subjected to alcohol precipitation is filtered to remove the insoluble matters, and concentrated under reduced pressure to obtain a plant extract as an extractum or dried to obtain a dry product.

In a second aspect, the present disclosure provides a plant extract obtained according to the above extraction method.

Preferably, the plant extract obtained according to the above extraction method of the present disclosure contains alkaloids with a weight content of 3% or more (preferably contains alkaloids with a weight content of 3% to 99%, more preferably contains alkaloids with a weight content of 15% to 99%, and further preferably contains alkaloids with a weight content of 45% to 99%, such as 35% to 70% or 60% to 75%), and/or contains polysaccharides with a weight content of no more than 70% (preferably contains polysaccharides with a weight content of 0.2% to 50%, and more preferably contains polysaccharides with a weight content of 0.2% to 35%), and/or contains flavones with a weight content of no more than 10% (preferably contains flavones with a weight content of 0.05% to 5%, and more preferably contains flavones with a weight content of 0.05% to 2%), and/or contains amino acids with a weight content of no more than 50% (preferably contains amino acids with a weight content of 0% to 40%, and more preferably contains amino acids with a weight content of 0% to 25%), and/or other components (with a weight content of preferably 0% to 25%, and more preferably 0% to 20%). The total content of each component is 100%, wherein "each component" refers to all components in the plant extract including alkaloids, polysaccharides, flavones and amino acids. That is, other components are contained in the plant extract in addition to alkaloids, polysaccharides, flavones and amino acids.

Preferably, the plant extract obtained by the above extraction method of the present disclosure contains each component in the following weight ratios:

| | |
|---|---|
| alkaloids | 3% to 99%; |
| polysaccharides | 0.2% to 70%; |
| flavones | 0% to 10%; |
| amino acids | 0% to 50%; |
| other components | 0% to 25%. |

Preferably, the plant extract obtained by the above extraction method of the present disclosure contains each component in the following weight ratios:

| | |
|---|---|
| alkaloids | 5% to 99%; |
| polysaccharides | 0.2% to 50%; |
| flavones | 0.05% to 5%; |
| amino acids | 0% to 40%; |
| other components | 0% to 20%. |

Further preferably, the plant extract obtained by the above extraction method of the present disclosure contains each component in the following weight ratios:

| | |
|---|---|
| alkaloids | 30% to 99%; |
| polysaccharides | 0.2% to 35%; |
| flavones | 0.05% to 2%; |
| amino acids | 0% to 25%; |
| other components | 0% to 20%. |

Preferably, the alkaloids contain 1-deoxynojirimycin (1-DNJ) with a weight content of 30% to 99%, preferably 50% to 95%, more preferably 55% to 90%, and more preferably 60% to 90%.

In a third aspect, the present disclosure provides a pharmaceutical composition comprising the above plant extract and an optional pharmaceutically acceptable excipient.

The excipient is an inactive component that conforms to the administration route or the mode of administration and has no toxic effect on the human body.

The excipient may be a solid excipient or a liquid excipient. Solid excipients, for example, include sodium lactate, poloxamer, sodium dodecyl sulfate, sodium carboxymethyl cellulose, gelatin, xanthan gum, povidone, starch, magnesium stearate, sodium carboxymethyl starch and talc. Liquid excipients, for example, include water, ethanol, syrup and glycerin.

Preferably, the dosage form of the pharmaceutical composition includes a preparation for oral administration.

Preferably, the dosage form of the pharmaceutical composition includes a tablet, a capsule, an oral solution, an oral emulsion, a pill and a granule.

Individual difference may exist in terms of the specific dosage of administration, depending on the patient's age, body weight, health condition, diet, administration route, drugs used in combination, treatment period, and the like.

In a fourth aspect, the present disclosure provides the use of the above plant extract or the above pharmaceutical composition in preparation of a hypoglycemic drug.

In another aspect, the present disclosure provides the use of the above plant extract or the above pharmaceutical composition in preparation of a drug for treating abnormal glucose tolerance.

In yet another aspect, the present disclosure provides the use of the above plant extract or the above pharmaceutical composition in preparation of a drug for preventing and/or treating a disease related to abnormal blood glucose. The diseases include but are not limited to diabetes, diabetic nephropathy, diabetes foot, eye complications caused by diabetes, hyperglycemia, hyperuricemia, hyperlipidemia, alteration of intestinal flora, and cardiovascular and cerebrovascular diseases such as cerebral infarction, cerebral hemorrhage, coronary heart disease, and hypertension.

The present disclosure further provides the use of the above plant extract or the above pharmaceutical composition in preparation of a lipid-lowing drug.

The present disclosure further provides the use of the above plant extract or the above pharmaceutical composition in preparation of a drug for regulating intestinal flora.

In still another aspect, the present disclosure provides a food, a health care product or a drink, comprising the above plant extract and an optional excipient acceptable for food, health care product or drink.

The present disclosure further provides the use of the above plant extract in preparation of a food, a health care product or a drink. Preferably, the food, the health care product or the drink is a food, a health care product or a drink with hypoglycemic effect.

The plant raw material of the present disclosure refers to the plant raw material used for extraction, including but not limited to fresh or processed plant or parts of the plant.

In the present disclosure, the crude plant extraction solution is subjected to treatment steps of resin separation, concentration and alcohol precipitation, which has the following beneficial effects as compared with the conventional extraction methods.

1. The content of heavy metal is significantly reduced.
2. The weight of the ethanol used in the conventional water extraction and alcohol precipitation method is ¼ to 5 times the weight of the charged plant raw material, while the amount of ethanol used in the extraction method of the present disclosure may be as low as 1/600 of the weight of the charged plant raw material, which greatly reduces the amount of ethanol used, reduces the production cost to a certain extent, facilitates industrial production, and improves the safety of the production process.

DETAILED DESCRIPTION

The present disclosure will be further described in detail with reference to the accompanying drawings and examples. The features and advantages of the present disclosure will become more clear and definite from these exemplary descriptions.

Herein the specific term "exemplary" means "used as an instance, or an example, or explanatory". Any "exemplary" example given here is not necessarily construed as being superior to or better than other examples.

In addition, the technical features involved in different embodiments of the present disclosure described below can be combined with one another as long as they are not in conflict with one another.

The present disclosure encompasses the following detection methods:

1. Content Determination of Alkaloids:

An appropriate amount of the extract was taken and added with water to dissolve it by ultrasound to prepare a test solution. Besides, an appropriate amount of 1-deoxynojirimycin was precisely weighed as a reference sample and added with water to dissolve it to prepare a reference solution. Appropriate volumes of the reference solution and the test solution were precisely measured respectively, added with sodium bicarbonate solutions, and mixed well by shaking. Thereafter, a solution of 9-fluorenylmethoxycarbonyl chloride (FMOC-Cl) in acetone was added and heated at 30° C. for 30 min. Acetic acid was added to terminate the reaction. The reactant was mixed well by shaking and filtered. A successive filtrate was precisely drawn and injected into a liquid chromatograph. According to the peak area, the content of the 1-deoxynojirimycin and the content of the total alkaloids in the test sample were calculated by the external standard method (calculating chromatographic peaks with the relative retention time in the range of 0.4 to 1.7, in terms of 1-deoxynojirimycin) (reference literature: Xuejun XIA, Renyun WANG, Yuling LIU. "Determination of mulberry twig alkaloids by RP-HPLC with pre-column derivatization" [J]. Chinese Journal of New Drugs, 2008, 17(23): 2044-2047).

2. Content Determination of Amino Acids:

An appropriate amount of the extract was taken and added with water to dissolve it by ultrasound to prepare a test solution. Besides, an appropriate amount of mixed amino acid was precisely weighed as a reference sample, and added with water to dissolve it to prepare a reference solution. The remaining operations were the same as those of the content determination of alkaloids.

3. Content Determination of Polysaccharides:

An appropriate amount of the extract was precisely weighed, added with water, extracted by ultrasound, and centrifuged at 4000 rpm for 10 min. A supernatant was taken as a test solution. 2 ml of the above test solution was measured, and put in a test tube with stopper, to which 6 ml of 0.1% anthrone-sulfuric acid reagent was added. The test tube was heated in a boiling water bath for 15 min, and left in an ice water bath for 15 min. The corresponding reagent was taken as a blank. The absorbance value was immediately measured at 625 nm. The concentration of the polysaccharides in the test sample relative to the glucose was calculated according to the glucose linear regression equation, and its content was calculated according to the following equation: Content=C*D*f/W, where W is the sample mass, C is the polysaccharide concentration relative to the glucose, f is the conversion factor (3.38), and D is the dilution factor (reference literature: Zuofa ZHANG, Jie JIN, Liangen SHI. "Method for content determination of polysaccharide in Ramulus Mori", China Journal of Chinese Materia Medica [J]. 2018, 33(4): 462-464).

4. Content Determination of Flavones:

An appropriate amount of the rutin reference sample was weighed, and dissolved with 60% ethanol to produce a rutin reference stock solution. 0.5 ml, 1.0 ml, 3.0 ml, 5.0 ml, and 7.0 ml of the rutin reference stock solutions were precisely measured respectively into 25-ml volumetric flasks, to which 10 ml of 5% sodium nitrite solution, 10% aluminum nitrate solution, and 1N NaOH solution were added respectively, and then diluted with water to the scale and mixed well by shaking as a reference solution. A blank reference solution was used as reference. The absorbance value was measured at 500 nm, and the linear regression equation was plotted.

An appropriate amount of the extract was precisely weighed, dissolved with 60% ethanol solution by ultrasound, mixed well by shaking, and centrifuged at 4000 rpm for 10 min. Thereafter, a supernatant was taken as a flavone extracting solution. 2.0 ml of the flavone extracting solutions were precisely measured, to which 10 ml of 5% sodium nitrite solution, 10% aluminum nitrate solution, and 1N NaOH solution were added respectively, then diluted with water to the scale, mixed well by shaking, left for 15 min, and centrifuged at 5000 rpm for 5 min. Afterwards, a supernatant was measured for determination. Another 2.0 ml of the flavone extracting solution was precisely measured, and diluted only with water to 25 ml as a blank reference solution in the case of no color reaction. The absorbance values of reaction solutions were measured at 500 nm. The flavone concentrations were calculated according to the linear regression equation. Then the flavone content in the test sample in terms of the rutin was calculated according to the sample weight and the dilution multiple.

5. Content Determination of Heavy Metals

The total content of the heavy metals was determined by the second method in the General Rules 0821 of Volume IV of the *Chinese Pharmacopoeia* 2015 *Edition*. The specific method was as follows:

(1) Preparation of Lead Standard Solution. 0.1599 g of lead nitrate was weighed and put in a 1000-nil volumetric flask. After dissolution with with 5 ml of nitric acid and 50 ml of water, the solution was diluted with water to the scale and mixed well by shaking as a stock solution. 0.5 ml, 1 ml, 2 ml, 5 ml, and 8 ml of the stock solutions were precisely measured respectively into 5-ml volumetric flasks, diluted with water to the scale, and mixed well by shaking, thereby obtaining 5 ppm, 10 ppm, 20 ppm, 30 ppm, 40 ppm, 50 ppm, and 80 ppm of lead standard solutions.

(2) Sample Assay. 2 g of the sample was taken, incinerated slowly until it was completely charred, cooled, wetted exactly with 0.5 to 1 ml of sulfuric acid, heated at a low temperature until the sulfuric acid was fully removed, added with 0.5 ml of nitric acid, then evaporated to dryness, cooled after nitric oxide vapor was fully removed, incinerated at 500° C. to 600° C. to make it completely ashed, cooled, added with 2 ml of hydrochloric acid, and evaporated to dryness on water bath followed by adding 15 ml of water. An ammonia solution was added dropwise until the phenolphthalein indicator solution became slightly pink, and then 2 ml of acetate buffer (pH3.5) was added. After the materials were dissolved with gentle heat, the solution was transferred to Nessler tubes and diluted with water to 25 ml as test tubes. Another reagent for formulating the test solution was taken and evaporated to dryness in a porcelain dish, then added with 2 ml of acetate buffer (pH3.5) and 15 ml of water, dissolved with gentle heat, thereafter transferred to Nessler tubes, to which a certain amount of the lead standard solution described in (1) was added respectively, and then diluted with water to 25 ml as reference tubes. Next, 2 ml of thioacetamide test solution was added to the test tubes and the reference tubes respectively, mixed well by shaking, left for 2 min, and placed on white paper at the same time. The test tubes and the reference tubes were observed in perspective from top to bottom. The color in the test tubes was compared with the color in the reference tubes to determine the content of heavy metals in the samples.

The content of the heavy metals lead, cadmium, mercury and arsenic could also be detected by the inductively coupled plasma mass spectrometry (ICP-MS method) described in the General Rules 0412 of Volume IV of the *Chinese Pharmacopoeia* 2015 *Edition*.

The detection results of the heavy metal content were compared with those documented in the *Green Trade Standards of Medicinal Plants and Preparations for Importing and Exporting*. The Standards stipulate that in plant materials, decoction pieces, extracts and preparations, the total content of heavy metals≤20.0 mg/kg, Pb≤5 mg/kg, Cd≤0.3 mg/kg, Hg≤0.2 mg/kg, Cu≤20.0 mg/kg, and As≤2.0 mg/kg.

The present inventors have compared the two methods for detecting heavy metals. The results show that the results of both methods are consistent, that is, the heavy metal content of the plant extracts obtained by the method of the present disclosure is in compliance with the provisions of the *Green Trade Standards of Medicinal Plants and Preparations for Importing and Exporting*. Preferably, the heavy metal content of the plant extracts obtained by the method of the present disclosure is not more than 20 ppm, more preferably not more than 10 ppm, and further preferably not more than 5 ppm.

Example 1

100 g of fresh mulberry (*Morus alba* L.) was taken and crushed, then added with 300 ml of alcohol water in 2 times, and extracted by heating reflux for 1 h each time. The extracting solutions were combined, and filtered to remove insoluble matters, thereby obtaining a crude extraction solution. The crude extraction solution was determined to contain 5 to 10 ppm of heavy metals, including 5.44 ppm of lead, 0.38 ppm of cadmium, 0.06 ppm of mercury, and 0.47 ppm of arsenic. The crude extraction solution was concentrated by heating until the solid content reached 2%, kept at 25° C., and served as a loading solution for the cation resin column.

5 g of 732-type strongly acidic styrene-based cation resin was filled in the column, washed with 2.5 mol/L hydrochloric acid solution until the pH of the eluate was 3.5; washed with 1.5 mol/L sodium hydroxide solution until the pH of the eluate was 8.0; washed with 2.5 mol/L hydrochloric acid solution until the pH of the eluate was 3.5; and then rinsed with 3 times column volume of deionized water to complete the activation. The concentrated extracting solution was loaded, and then eluted with 3 L of 0.1 mol/L ammonia water at an elution speed of 10 BV/h. The eluate was collected when the effluent from the cation resin column was detected to be at pH>7. When the collection solution was up to 1 L, the collection was stopped. The collection solution was purified directly over the anion resin column.

1.25 g of D218-type macroporous and strongly alkaline acrylic-based anion resin was filled in the column, washed with 1.5 mol/L sodium hydroxide solution until the pH of the eluate was 9.0; washed with 1.5 mol/L hydrochloric acid solution until the pH of the eluate was 3.5; and washed with 1.5 mol/L sodium hydroxide solution until the pH of the eluate was 9.0; and the activation was completed. The eluate collected from the cation resin was loaded onto the anion resin. The effluent was collected and the collection was terminated when the effluent was up to 1 L.

The collection solution resulting from the separation via the anion resin column was centrifuged to remove impurities, and then concentrated through the reverse osmosis membrane. The specific gravity of the concentrated liquid was 1.0. It was transferred to an alcohol precipitation tank, and 25 g of anhydrous ethanol was added when the stirring paddle was at 100 rpm. After adding the ethanol, the solution was stopped stirring, and subjected to alcohol precipitation for 24 h. The supernatant was taken and vacuum dried to obtain an extract.

In addition, fresh Ramulus Mori, Cortex Mori, and Folium Mori (*Monrus alba* L.) were prepared and extracted. The extraction method and parameters were as same as those described above. The heavy metal content in the crude extraction solutions obtained from Ramulus Mori, Cortex Mori, and Folium Mori was all 5 to 10 ppm, in which the lead content was 5.51, 5.87, and 6.12 ppm respectively, the cadmium content was 0.37, 0.35, and 0.41 ppm respectively, the mercury content was 0.07, 0.08, and 0.06 ppm respectively, and the arsenic content was 0.57, 0.55, and 0.61 ppm respectively.

The content of the components and the content of the heavy metals in the resulting mulberry, Ramulus Mori, Cortex Mori, and Folium Mori extracts were listed in Table 1.

determined to contain 10 to 20 ppm of heavy metals, including 13.6 ppm of lead, 0.84 ppm of cadmium, 0.16 ppm of mercury, and 0.56 ppm of arsenic. The crude extraction solution was centrifuged to remove impurities and then concentrated by filtering through the reverse osmosis membrane until the solid content reached 14.5%. The concentrated crude extraction solution was transferred to an alcohol precipitation tank, and 80 g (about 100 ml) of anhydrous ethanol was added when the stirring paddle was at 300 rpm. After adding the ethanol, the solution was stopped stirring, and subjected to alcohol precipitation for 24 h. The supernatant was taken as a loading solution for the cation resin column.

10 g of 734-type strongly acidic styrene-based cation resin was filled in the column, washed with 2 mol/L hydrochloric acid solution until the pH of the eluate was 4.5; washed with 1 mol/L sodium hydroxide solution until the pH of the eluate was 8.5; washed with 2 mol/L hydrochloric acid solution until the pH of the eluate was 4.5; and then rinsed with 5 times column volume of deionized water to complete the activation. The extracting solution after concentration and alcohol precipitation was loaded, and then eluted with 2 L of 0.5 mol/L ammonia water at an elution speed of 8 BV/h. The eluate was collected when the effluent from the cation resin column was detected to be at pH>7. When the collection solution was up to 800 ml, the collection was stopped. The collection solution was purified directly over the anion resin column.

8 g of 717-type strongly alkaline styrene-based anion resin was filled in the column, washed with 1.5 mol/L sodium hydroxide solution until the pH of the eluate was 9.0; washed with 1.5 mol/L hydrochloric acid solution until the pH of the eluate was 3.5; and washed with 1.5 mol/L sodium hydroxide solution until the pH of the eluate was 9.0 to complete the activation. The eluate collected from the cation resin was loaded onto the anion resin. The effluent

TABLE 1

Content of Components and Content of Heavy Metals in Plant Extracts Obtained in Example 1

| Content | Extract | | | |
| --- | --- | --- | --- | --- |
| | Mulberry Extract | Ramulus Mori Extract | Cortex Mori Extract | Folium Mori Extract |
| Alkaloids % | 45 | 48 | 45 | 30 |
| Polysaccharides % | 28 | 25 | 27 | 34 |
| Flavones % | 5 | 4 | 6 | 7 |
| Amino acid % | 20 | 17 | 18 | 30 |
| 1-DNJ % in alkaloids | 60 | 62 | 61 | 55 |
| Total heavy metal content (ppm) | <5 | <5 | <5 | <5 |
| Pb (ppm) | 0.74 | 0.70 | 0.67 | 0.66 |
| Cd (ppm) | 0.05 | 0.05 | 0.04 | 0.04 |
| Hg (ppm) | 0.02 | 0.01 | 0.02 | 0.01 |
| As (ppm) | 0.17 | 0.12 | 0.13 | 0.15 |

Example 2

100 g of fresh Folium Mori (*Morus atropurpurea* Roxb) was taken and crushed, then added with 2000 ml of acid water in 2 times, and extracted by the decocting method for 1 h each time. The extracting solutions were combined, and filtered to remove insoluble matters, thereby obtaining a crude extraction solution. The crude extraction solution was was collected and the collection was terminated when the effluent was up to 750 ml.

The collection solution resulting from the separation via the anion resin column was concentrated by heating. The specific gravity of the concentrated liquid was 1.05. It was transferred to an alcohol precipitation tank, and 12.5 g of anhydrous ethanol was added when the stirring paddle was at 200 rpm. After adding the ethanol, the solution was stopped stirring, and subjected to alcohol precipitation for 24 h. The supernatant was taken and vacuum dried to obtain an extract.

In addition, fresh Ramulus Mori and Cortex Mori (*Morus atropurpurea* Roxb) were prepared and extracted. The extraction method and parameters were as same as those described above. The heavy metal content in the crude extraction solutions obtained from Ramulus Mori and Cortex Mori was both 10 to 20 ppm, in which the lead content was 14.5 and 15.8 ppm respectively, the cadmium content was 0.78 and 0.77 ppm respectively, the mercury content was 0.17 and 0.18 ppm respectively, and the arsenic content was 0.57 and 0.55 ppm respectively.

The content of the components and the content of the heavy metals in the resulting Ramulus Mori, Cortex Mori, and Folium Mori extracts were listed in Table 2.

TABLE 2

Content of Components and Content of Heavy Metals in Plant Extracts Obtained in Example 2

| Content | Extract | | |
|---|---|---|---|
| | Ramulus Mori Extract | Cortex Mori Extract | Folium Mori Extract |
| Alkaloids % | 80 | 75 | 60 |
| Polysaccharides % | 10 | 14 | 17 |
| Flavones % | 0.3 | 0.4 | 0.5 |
| Amino acid % | 5 | 6 | 18 |
| 1-DNJ % in alkaloids | 75 | 69 | 70 |
| Total heavy metal content (ppm) | <5 | <5 | <5 |
| Pb (ppm) | 0.65 | 0.73 | 1.13 |
| Cd (ppm) | 0.03 | 0.02 | 0.08 |
| Hg (ppm) | 0.01 | 0.02 | 0.09 |
| As (ppm) | 0.11 | 0.10 | 0.25 |

Example 3

1000 kg of fresh Ramulus Mori (Yuesang No. 11) was taken and crushed, then added with 4000 L of water, and extracted by heating reflux for 2 h. The extracting solutions were combined, and filtered to remove insoluble matters, thereby obtaining a crude extraction solution. The crude extraction solution was determined to contain 40 to 80 ppm of heavy metals, including 52 ppm of lead, 1.94 ppm of cadmium, 0.88 ppm of mercury, and 1.11 ppm of arsenic. The crude extraction solution was concentrated by heating until the solid content reached 4%, kept at 50° C., and served as a loading solution for the cation resin column.

150 kg of D113-type macroporous and weakly acidic phenylpropene-based cation resin was filled in the column, washed with 2 mol/L hydrochloric acid solution until the pH of the eluate was 4.5; washed with 1 mol/L sodium hydroxide solution until the pH of the eluate was 8.5; washed with 2 mol/L hydrochloric acid solution until the pH of the eluate was 4.5; and then rinsed with 5 times column volume of deionized water to complete the activation. The concentrated extracting solution was loaded, and then eluted with 1000 L of 2.5 mol/L ammonia water at an elution speed of 6 BV/h. The eluate was collected when the effluent from the cation resin column was detected to be at pH>7. When the collection solution was up to 900 L, the collection was stopped. The collection solution was purified directly over the anion resin column.

62.5 kg of D218-type macroporous and strongly alkaline acrylic-based anion resin was filled in the column, washed with 1.5 mol/L sodium hydroxide solution until the pH of the eluate was 9.0; washed with 1.5 mol/L hydrochloric acid solution until the pH of the eluate was 3.5; and washed with 1.5 mol/L sodium hydroxide solution until the pH of the eluate was 9.0 to complete the activation. The eluate collected from the cation resin was loaded onto the anion resin. The effluent was collected and the collection was terminated when the effluent was up to 870 L.

The collection solution resulting from the separation via the anion resin column was filtered via a micro-filtration membrane to remove impurities, and then concentrated through the reverse osmosis membrane. The specific gravity of the concentrated liquid was 1.1. It was transferred to an alcohol precipitation tank, and 15 kg of anhydrous ethanol was added when the stirring paddle was at 400 rpm. After adding the ethanol, the solution was stopped stirring, and subjected to alcohol precipitation for 24 h. The supernatant was taken and concentrated under reduced pressure to obtain an extractum.

In addition, fresh Cortex Mori and Folium Mori (Yuesang No. 11) were prepared and extracted. The extraction method and parameters were as same as those described above. The heavy metal content in the crude extraction solutions obtained from Cortex Mori and Folium Mori was both 40 to 80 ppm, in which the lead content was 48 and 53 ppm respectively, the cadmium content was 1.78 and 1.77 ppm respectively, the mercury content was 0.77 and 0.78 ppm respectively, and the arsenic content was 0.87 and 0.95 ppm respectively.

The content of the components and the content of the heavy metals in the resulting Ramulus Mori, Cortex Mori, and Folium Mori extractums were listed in Table 3.

TABLE 3

Content of Components and Content of Heavy Metals in Plant Extracts Obtained in Example 3

| Content | Extract | | |
|---|---|---|---|
| | Ramulus Mori Extract | Cortex Mori Extract | Folium Mori Extract |
| Alkaloids % | 75 | 67 | 50 |
| Polysaccharides % | 15 | 20 | 27 |
| Flavones % | 0.7 | 0.8 | 3 |
| Amino acid % | 5 | 6 | 16 |
| 1-DNJ % in alkaloids | 72 | 70 | 66 |
| Total heavy metal content (ppm) | <5 | <5 | <5 |
| Pb (ppm) | 2.71 | 2.65 | 2.60 |
| Cd (ppm) | 0.03 | 0.06 | 0.05 |
| Hg (ppm) | 0.24 | 0.10 | 0.12 |
| As (ppm) | 0.72 | 0.45 | 0.50 |

Example 4

1000 kg of air dried Cortex Mori (Guisangyou No. 62) was taken and crushed, then added with 10000 L of water in 2 times, and extracted by heating reflux for 2.5 h each time. The extracting solutions were combined, and filtered to remove insoluble matters, thereby obtaining a crude extraction solution. The crude extraction solution was determined to contain less than 5 ppm of heavy metals, including 1.57 ppm of lead, 0.23 ppm of cadmium, 0.09 ppm of mercury, and 0.58 ppm of arsenic. The crude extraction solution was filtered via a micro-filtration membrane to remove impurities, and then concentrated through the reverse osmosis membrane until the solid content reached 6%, and served as a loading solution for the cation resin column.

100 kg of D001-type macroporous and strongly acidic styrene-based cation resin was filled in the column. The cation resin was activated according to the method described in Example 3. The concentrated extracting solution was loaded, and then eluted with 500 L of 0.2 mol/L ammonium chloride at an elution speed of 5 BV/h. The effluent was detected with 20% silicotungstic acid, and started to collect when a white precipitate was generated. The collection was terminated when the collection solution reached 200 L. The collection solution was purified directly over the anion resin column.

32 kg of D201-type macroporous and strongly alkaline styrene-based anion resin was filled in the column. The anion resin was activated according to the method described in Example 3. The eluate collected from the cation resin column was loaded onto the anion resin. The effluent was collected and the collection was terminated when the effluent was up to 100 L.

The collection solution resulting from the separation via the anion resin column was concentrated by heating. The specific gravity of the concentrated liquid was 1.2. It was transferred to an alcohol precipitation tank, and 3 kg of anhydrous ethanol was added when the stirring paddle was at 350 rpm. After adding the ethanol, the solution was stopped stirring, and subjected to alcohol precipitation for 24 h. The supernatant was taken and concentrated under reduced pressure to obtain an extractum.

In addition, air dried Ramulus Mori (Guisangyou No. 62) was prepared and extracted. The extraction method and parameters were as same as those described above. The crude extraction solution obtained from the Ramulus Mori contained 5 to 10 ppm of heavy metals, in which the lead content was 1.66 ppm respectively, the cadmium content was 0.25 ppm respectively, the mercury content was 0.07 ppm respectively, and the arsenic content was 0.60 ppm respectively.

The content of the components and the content of the heavy metals in the resulting Ramulus Mori and Cortex Mori extractums were listed in Table 4.

TABLE 4

Content of Components and Content of Heavy Metals in Plant Extracts Obtained in Example 4

| Content | Ramulus Mori Extract | Cortex Mori Extract |
| --- | --- | --- |
| Alkaloids % | 65 | 58 |
| Polysaccharides % | 16 | 20 |
| Flavones % | 0.7 | 0.5 |
| Amino acid % | 17 | 20 |
| 1-DNJ % in alkaloids | 69 | 68 |
| Total heavy metal content (ppm) | <5 | <5 |
| Pb (ppm) | 0.08 | 0.04 |
| Cd (ppm) | 0.04 | 0 |
| Hg (ppm) | 0.01 | 0.01 |
| As (ppm) | 0.21 | 0.16 |

Example 5

10 kg of fresh Ramulus Mori (Sangteyou No. 2) was taken and crushed, then added with 150 L water in 2 times, and extracted by the decocting method for 3 h each time. The extracting solutions were combined, and filtered to remove the insoluble matters. The extracting solution was concentrated by heating until the solid content reached 8%. It was transferred to an alcohol precipitation tank. 2367.9 g of anhydrous ethanol (3 L) was added when the stirring paddle was at 300 rpm. After adding the ethanol, the solution was stopped stirring, and subjected to alcohol precipitation for 24 h. The supernatant was taken as a loading solution for the cation resin column.

5 kg of 002SC-type strongly acidic styrene-based cation resin was filled in the column. The cation resin was activated according to the method described in Example 3. The extracting solution after concentration and alcohol precipitation was loaded, and then eluted with 100 L of 5 mol/L potassium chloride at an elution speed of 5 BV/h. The effluent was detected with 20% silicotungstic acid, and started to collect when a white precipitate was generated. The collection was terminated when the collection solution reached 25 L. The collection solution was purified directly over the anion resin column.

10 kg of 711-type strongly alkaline styrene-based anion resin was filled in the column. The anion resin was activated according to the method described in Example 3. The eluate collected from the cation resin was loaded onto the anion resin. The effluent was collected and the collection was terminated when the effluent was up to 15 L. The collection solution was reloaded onto the cation resin, and separated twice via the cation resin and anion resin in sequence according to the methods described above.

The collection solution obtained after three column separation was centrifuged to remove impurities, and then concentrated through a reverse osmosis membrane. The specific gravity of the concentrated liquid was 1.25. It was transferred to an alcohol precipitation tank, and 125 g of anhydrous ethanol was added when the stirring paddle was at 1000 rpm. After adding the ethanol, the solution was stopped stirring, and subjected to alcohol precipitation for 24 h. The supernatant was taken and concentrated under reduced pressure to obtain an extractum. In addition, fresh Cortex Mori and Folium Mori (Sangteyou No. 2) were prepared and extracted. The extraction method and parameters were as same as those described above. The content of the components and the content of the heavy metals in the resulting Ramulus Mori, Cortex Mori, and Folium Mori extractums were listed in Table 5.

TABLE 5

Content of Components and Content of Heavy Metals in Plant Extracts Obtained in Example 5

| Content | Ramulus Mori Extract | Cortex Mori Extract | Folium Mori Extract |
| --- | --- | --- | --- |
| Alkaloids % | 98 | 95 | 90 |
| Polysaccharides % | 0.2 | 2 | 4 |
| Flavones % | 0.05 | 0.1 | 0.1 |
| Amino acid % | 0 | 1 | 3 |
| 1-DNJ % in alkaloids | 99 | 96 | 91 |
| Total heavy metal content (ppm) | <5 | <5 | <5 |
| Pb (ppm) | 0.06 | 0.05 | 0.07 |
| Cd (ppm) | 0 | 0 | 0 |
| Hg (ppm) | 0 | 0 | 0.01 |
| As (ppm) | 0.16 | 0.12 | 0.15 |

Example 6

1 kg of fresh mulberry root (Yuesang No. 11) was taken and crushed, then added with 6 L alcohol water in 3 times, and extracted by ultrasonic extraction for 1 h each time. The extracting solutions were combined, and filtered to remove the insoluble matters to obtain a crude extraction solution. The crude extraction solution served as a loading solution for the cation resin column.

1 kg of D254-type macroporous and strongly alkaline quaternary ammonium-type cation resin was filled in the column. The cation resin was activated according to the method described in Example 3. The crude extraction solution was loaded, and then eluted with 15 L of 3 mol/L sodium chloride at an elution speed of 5 BV/h. The effluent was detected with 20% silicotungstic acid, and started to collect when a white precipitate was generated. The collection was terminated when the collection solution reached 5 L. The collection solution was purified directly over the anion resin column.

1 kg of D301-type macroporous and weakly alkaline styrene-based anion resin was filled in the column. The anion resin was activated according to the method described in Example 3. The eluate collected from the cation resin was loaded onto the anion resin. The effluent was collected and the collection was terminated when the effluent was up to 5 L. The collection solution was reloaded onto the cation resin, and separated again via the cation resin and anion resin successively according to the methods described above.

The collection solution resulting from two column separation was centrifuged to remove impurities, and then concentrated through a reverse osmosis membrane. The specific gravity of the concentrated liquid was 1.2. It was transferred to an alcohol precipitation tank, and 6.3 g of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum. In addition, fresh Ramulus Mori and Folium Mori (Yuesang No. 11) were prepared and extracted. The extraction method and parameters were as same as those described above. The content of the components and the content of the heavy metals in the resulting Ramulus Mori, Folium Mori, and mulberry root extractums were listed in Table 6.

TABLE 6

Content of Components and Content of Heavy Metals in Plant Extracts Obtained in Example 6

| Content | Ramulus Mori Extract | Folium Mori Extract | Mulberry Root Extract |
|---|---|---|---|
| Alkaloids % | 97 | 85 | 92 |
| Polysaccharides % | 0.3 | 5 | 3 |
| Flavones % | 0.06 | 0.3 | 0.1 |
| Amino acid % | 0 | 5 | 2 |
| 1-DNJ % in alkaloids | 98 | 83 | 95 |
| Total heavy metal content (ppm) | <5 | <5 | <5 |
| Pb (ppm) | 0.05 | 0.03 | 0.05 |
| Cd (ppm) | 0 | 0 | 0 |
| Hg (ppm) | 0 | 0.02 | 0 |
| As (ppm) | 0.13 | 0.14 | 0.14 |

Example 7

1000 kg of fresh Ramulus Mori (Moms atropurpurea Roxb) was taken and crushed, then added with 11500 L water, and extracted by heating reflux for 2 h. The extracting solutions were combined, and filtered to remove the insoluble matters to obtain a crude extraction solution. The crude extraction solution was centrifuged to remove impurities, then concentrated through a reverse osmosis membrane until the solid content reached 1%, and served as a loading solution for the cation resin column.

150 kg of D001-type macroporous and strongly acidic styrene-based cation resin was filled in the column. The cation resin was activated according to the method described in Example 3. The concentrated crude extraction solution was loaded, and eluted with 5000 L of 0.04 mol/L ammonium nitrate at an elution speed of 5 BV/h. The effluent was detected with 20% silicotungstic acid, and started to collect when a white precipitate was generated. The collection was terminated when the collection solution reached 1000 L.

The collection solution resulting from the cation resin column separation was concentrated through a nanofiltration membrane. The specific gravity of the concentrated liquid was 1.3. It was transferred to an alcohol precipitation tank, and 1.7 kg of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In addition, fresh Cortex Mori and Folium Mori (*Morus atropurpurea* Roxb) were prepared and extracted. The extraction method and parameters were as same as those described above. The content of the components and the content of the heavy metals in the resulting Ramulus Mori, Cortex Mori, and Folium Mori extractums were listed in Table 7.

TABLE 7

Content of Components and Content of Heavy Metals in Plant Extracts Obtained in Example 7

| Content | Ramulus Mori Extract | Cortex Mori Extract | Folium Mori Extract |
|---|---|---|---|
| Alkaloids % | 15 | 10 | 8 |
| Polysaccharides % | 40 | 42 | 45 |
| Flavones % | 0.7 | 0.8 | 0.6 |
| Amino acid % | 40 | 41 | 43 |
| 1-DNJ % in alkaloids | 55 | 50 | 49 |
| Total heavy metal content (ppm) | <5 | <5 | <5 |
| Pb (ppm) | 0.12 | 0.10 | 0.09 |
| Cd (ppm) | 0 | 0 | 0 |
| Hg (ppm) | 0.02 | 0.02 | 0.01 |
| As (ppm) | 0.18 | 0.11 | 0.15 |

Example 8

1000 kg of fresh Ramulus Mori (Yuesang No. 11) was taken and crushed, then added with 8000 L water in 2 times, and extracted by the decocting method for 2 h each time. The extracting solutions were combined, and filtered to remove the insoluble matters to obtain a crude extraction solution. The crude extraction solution was filtered via a microfiltration membrane to remove impurities, then concentrated through a reverse osmosis membrane until the solid content reached 1%, and served as a loading solution for the cation resin column.

41.7 kg of 732-type strongly acidic styrene-based cation resin was filled in the column. The cation resin was activated according to the method described in Example 3. The crude extraction solution was loaded, and eluted with 1000 L of 0.1 mol/L sodium chloride at an elution speed of 5 BV/h. The effluent was detected with 20% silicotungstic acid, and started to collect when a white precipitate was generated. The collection was terminated when the collection solution reached 500 L.

The collection solution resulting from the cation resin column separation was concentrated via a nanofiltration membrane. The specific gravity of the concentrated liquid was 1.25. It was transferred to an alcohol precipitation tank, and 15 kg of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In addition, fresh Cortex Mori and Folium Mori (Yuesang No. 11) were prepared and extracted. The extraction method and parameters were as same as those described above. The content of the components and the content of the heavy metals in the resulting Ramulus Mori, Cortex Mori, and Folium Mori extractums were listed in Table 8.

TABLE 8

Content of Components and Content of Heavy Metals in Plant Extracts Obtained in Example 8

| Content | Extract | | |
|---|---|---|---|
| | Ramulus Mori Extract | Cortex Mori Extract | Folium Mori Extract |
| Alkaloids % | 10 | 8 | 5 |
| Polysaccharides % | 44 | 50 | 60 |
| Flavones % | 1 | 1.2 | 2 |
| Amino acid % | 41 | 37 | 30 |
| 1-DNJ % in alkaloids | 54 | 45 | 46 |
| Total heavy metal content (ppm) | <5 | <5 | <5 |
| Pb (ppm) | 0.55 | 0.30 | 0.43 |
| Cd (ppm) | 0.02 | 0.01 | 0.02 |
| Hg (ppm) | 0.03 | 0.01 | 0.01 |
| As (ppm) | 0.11 | 0.10 | 0.12 |

Example 9

100 g of fresh Ramulus Mori (*Morus atropurpurea* Roxb) was taken and crushed, then added with 600 ml water, extracted by heating reflux for 1 h, and filtered to remove the insoluble matters to obtain a crude extraction solution. The crude extraction solution was first concentrated by heating until the solid content reached 5%, and used as a loading solution for the cation resin column.

3.85 g of 732-type strongly acidic styrene-based cation resin was filled in the column. The cation resin was activated according to the method described in Example 3. The crude extraction solution was loaded, and eluted with 700 mL of 0.15 mol/L ammonium chloride at an elution speed of 5 BV/h. The effluent was detected with 20% silicotungstic acid, and started to collect when a white precipitate was generated. The collection was terminated when the collection solution reached 100 mL.

The collection solution resulting from the cation resin column separation was concentrated by heating. The specific gravity of the concentrated liquid was 1.3. It was transferred to an alcohol precipitation tank, and 25 g of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In addition, fresh Cortex Mori and Folium Mori (*Morus atropurpurea* Roxb) were prepared and extracted. The extraction method and parameters were as same as those described above. The content of the components and the content of the heavy metals in the resulting Ramulus Mori, Cortex Mori, and Folium Mori extractums were listed in Table 9.

TABLE 9

Content of Components and Content of Heavy Metals in Plant Extracts Obtained in Example 9

| Content | Extract | | |
|---|---|---|---|
| | Ramulus Mori Extract | Cortex Mori Extract | Folium Mori Extract |
| Alkaloids % | 8 | 5 | 3 |
| Polysaccharides % | 45 | 48 | 50 |
| Flavones % | 1.5 | 2 | 3 |
| Amino acid % | 40 | 40 | 41 |
| 1-DNJ % in alkaloids | 44 | 40 | 38 |
| Total heavy metal content (ppm) | <5 | <5 | <5 |
| Pb (ppm) | 0.70 | 0.67 | 0.60 |
| Cd (ppm) | 0.01 | 0.02 | 0.01 |
| Hg (ppm) | 0.01 | 0.02 | 0.01 |
| As (ppm) | 0.14 | 0.10 | 0.11 |

Example 10

1000 kg of fresh Ramulus Mori (Sangteyou No. 2) was taken and crushed, then added with 5000 L water, extracted by heating reflux for 1 h, and filtered to remove the insoluble matters to obtain a crude extraction solution. The crude extraction solution was first concentrated by heating until the solid content reached 10%, and used as a loading solution for the cation resin column.

3.5 g of D254 macroporous and strongly alkaline quaternary ammonium-type cation resin was filled in the column. The cation resin was activated according to the method described in Example 3. The crude extraction solution was loaded, and then eluted with 200 L of 0.15 mol/L potassium chloride at an elution speed of 5 BV/h. The effluent was detected with 20% silicotungstic acid, and started to collect when a white precipitate was generated. The collection was terminated when the collection solution reached 100 L.

The collection solution resulting from the cation resin column separation was concentrated by heating. The specific gravity of the concentrated liquid was 1.05. It was transferred to an alcohol precipitation tank, and 15 kg of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In addition, fresh Cortex Mori (Sangteyou No. 2) was prepared and extracted. The extraction method and parameters were as same as those described above. The content of the components and the content of the heavy metals in the resulting Ramulus Mori, Cortex Mori extractums were listed in Table 10.

TABLE 10

Content of Components and Content of Heavy Metals in Plant Extracts Obtained in Example 10

| Content | Extract | |
|---|---|---|
| | Ramulus Mori Extract | Cortex Mori Extract |
| Alkaloids % | 5 | 3 |
| Polysaccharides % | 47 | 50 |
| Flavones % | 2 | 3 |
| Amino acid % | 41 | 41 |
| 1-DNJ % in alkaloids | 47 | 43 |
| Total heavy metal content (ppm) | <5 | <5 |
| Pb (ppm) | 0.24 | 0.27 |
| Cd (ppm) | 0 | 0 |
| Hg (ppm) | 0.01 | 0.02 |
| As (ppm) | 0.12 | 0.14 | above. The content of the components and the content of the heavy metals in the resulting Ramulus Mori, Cortex Mori, and Folium Mori extractums were listed in Table 11.

TABLE 11

Content of Components and Content of Heavy Metals in Plant Extracts Obtained in Example 11

| Content | Extract | | |
|---|---|---|---|
| | Ramulus Mori Extract | Cortex Mori Extract | Folium Mori Extract |
| Alkaloids % | 30 | 30 | 15 |
| Polysaccharides % | 31 | 34 | 40 |
| Flavones % | 3 | 2 | 1 |
| Amino acid % | 30 | 28 | 39 |
| 1-DNJ % in alkaloids | 58 | 55 | 53 |
| Total heavy metal content (ppm) | <5 | <5 | <5 |
| Pb (ppm) | 0.26 | 0.30 | 0.25 |
| Cd (ppm) | 0.01 | 0.02 | 0.01 |
| Hg (ppm) | 0.01 | 0 | 0.02 |
| As (ppm) | 0.11 | 0.12 | 0.13 |

Example 11

1000 g of fresh Ramulus Mori (*Morus bombycis* Koidz.) was taken and crushed, then added with 10 L acid water in 3 times, extracted by ultrasound for 2 h each time, and filtered to remove the insoluble matters to obtain a crude extraction solution. The crude extraction solution was filtered via a micro-filtration membrane to remove impurities, then concentrated through a reverse osmosis membrane until the solid content reached 4%, and used as a loading solution for the cation resin column.

66.67 g of D001-type macroporous and strongly acidic styrene-based cation resin was filled in the column. The cation resin was activated according to the method described in Example 3. The crude extraction solution was loaded, and then eluted with 12 L of 1.5 mol/L ammonia water at an elution speed of 5 BV/h. The eluate was collected when the effluent from the cation resin column was detected by the high performance liquid chromatography to contain alkaloids. The collection was terminated when the collection solution was up to 100 mL. The collection solution was purified directly over the anion resin column.

13.3 g of D218-type macroporous and strongly alkaline styrene-based anion resin was filled in the column. The anion resin was activated according to the method described in Example 3. The eluate collected from the cation resin was loaded onto the anion resin column. The effluent was collected and the collection was terminated when the effluent was up to 50 ml.

The collection solution resulting from the anion resin column separation was filtered via a micro-filtration membrane to remove impurities and then concentrated through a reverse osmosis membrane. The specific gravity of the concentrated liquid was 1.15. It was transferred to an alcohol precipitation tank, and 25 g of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In addition, fresh Cortex Mori and Folium Mori (*Morus bombycis* Koidz.) were prepared and extracted. The extraction method and parameters were as same as those described Example 12

100 g of fresh Cortex Mori (Guisangyou No. 62) was taken and crushed, then added with 1.2 L alcohol water, extracted by the decocting method for 1 h, and filtered to remove the insoluble matters to obtain a crude extraction solution. The crude extraction solution was first concentrated by heating until the solid content reached 8%, and used as a loading solution for the cation resin column.

33.34 g of 734-type strongly acidic styrene-based cation resin was filled in the column. The cation resin was activated according to the method described in Example 3. The crude extraction solution was loaded, and then eluted with 50 mL of 2.5 mol/L ammonia water at an elution speed of 5 BV/h. The eluate was collected when the effluent from the cation resin column was detected to be at pH>7. The collection was terminated when the collection solution was up to 10 mL.

The collection solution resulting from the cation resin column separation was centrifuged to remove impurities, and then concentrated through the reverse osmosis membrane. The specific gravity of the concentrated liquid was 1.2. It was transferred to an alcohol precipitation tank, and 15 g of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In the Cortex Mori extractum, the alkaloid content was 15%, the polysaccharide content was 38%, the flavone content was 2%, and the amino acid content was 40%. In the alkaloids, the 1-DNJ content was 52%.

The total heavy metal content was less than 5 ppm, including 0.29 ppm of lead, 0 ppm of cadmium, 0.02 ppm of mercury, and 0.10 ppm of arsenic.

Example 13

100 g of fresh Ramulus Mori (*Morus alba* L.) was taken and crushed, then added with 300 ml alkaline water, extracted by heating reflux for 0.5 h, and filtered to remove the insoluble matters to obtain a crude extraction solution. The crude extraction solution was centrifuged to remove impurities, then concentrated through a reverse osmosis membrane until the solid content reached 6%, and used as a loading solution for the cation resin column.

3.34 g of 732-type strongly acidic styrene-based cation resin was filled in the column. The cation resin was activated according to the method described in Example 3. The crude extraction solution was loaded, and then eluted with 3 L of 1.0 mol/L ammonia water at an elution speed of 5 BV/h. The effluent was detected with 20% silicotungstic acid, and started to collect when a white precipitate was generated. The collection was terminated when the collection solution reached 400 mL.

The collection solution resulting from the cation resin column separation was concentrated by heating. The specific gravity of the concentrated liquid was 1.25. It was transferred to an alcohol precipitation tank, and 5 g of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In the resulting Ramulus Mori extractum, the alkaloid content was 3%, the polysaccharide content was 60%, the flavone content was 5%, and the amino acid content was 30%. In the alkaloids, the 1-DNJ content was 47%.

The total heavy metal content was less than 5 ppm, including 0.31 ppm of lead, 0 ppm of cadmium, 0.01 ppm of mercury, and 0.14 ppm of arsenic.

Example 14

100 g of fresh Folium Mori (*Morus* multicaulis Perrott.) was taken and crushed, then added with 500 ml of alcohol water, extracted by the decocting method for 0.5 h, and filtered to remove the insoluble matters to obtain a crude extraction solution. The crude extraction solution was concentrated via a nanofiltration membrane until the solid content reached 12%, and used as a loading solution for the cation resin column.

25 g of 732-type strongly acidic styrene-based cation resin was filled in the column. The cation resin was activated according to the method described in Example 3. The crude extraction solution was loaded, and then eluted with 2 L of 2.0 mol/L ammonia water at an elution speed of 5 BV/h. The eluate was collected when the effluent from the cation resin column was detected by the high performance liquid chromatography to contain alkaloids. The collection was terminated when the collection solution was up to 800 mL.

The collection solution resulting from the cation resin column separation was concentrated by heating. The specific gravity of the concentrated liquid was 1.14. It was transferred to an alcohol precipitation tank, and 5 g of anhydrous ethanol was added when the stirring paddle was at 600 rpm. After adding the ethanol, the solution was stopped stirring, and subjected to alcohol precipitation for 24 h. The supernatant was taken and concentrated under reduced pressure to obtain an extractum.

In the resulting Folium Mori extractum, the alkaloid content was 10%, the polysaccharide content was 43%, the flavone content was 1%, and the amino acid content was 37%. In the alkaloids, the 1-DNJ content was 50%.

The total heavy metal content was less than 5 ppm, including 0.33 ppm of lead, 0.01 ppm of cadmium, 0.02 ppm of mercury, and 0.15 ppm of arsenic.

Example 15

100 g of fresh *Hyacinthus orientalis* (*Hyacinthus orientalis*) bulbs were taken and crushed, then added with 700 ml of water in 2 times, and extracted by ultrasound for 0.5 h. The extracting solutions were combined, and filtered to remove the insoluble matters to obtain a crude extraction solution. The crude extraction solution was concentrated via a nanofiltration membrane until the solid content reached 10%, and used as a loading solution for the cation resin column.

3.5 g of 732-type strongly acidic styrene-based cation resin was filled in the column. The cation resin was activated according to the method described in Example 3. The concentrated crude extraction solution was loaded, and eluted with 10 ml of 1.75 mol/L sodium hydroxide solution at an elution speed of 10 BV/h. The eluate was collected when the effluent from the cation resin column was detected to be at pH>7. The collection was terminated when the collection solution was up to 10 ml. The collection solution was purified directly over the anion resin column.

4 g of D218-type macroporous and strongly alkaline styrene-based anion resin was filled in the column. The anion resin was activated according to the method described in Example 3. The eluate collected from the cation resin was loaded onto the anion resin. The effluent was collected and the collection was terminated when the effluent was up to 5 ml.

The collection solution resulting from the separation via the anion resin column was concentrated by heating. The specific gravity of the concentrated liquid was 1.1. It was transferred to an alcohol precipitation tank, and 0.4 g of anhydrous ethanol was added when the stirring paddle was at 100 rpm. After adding the ethanol, the solution was stopped stirring, and subjected to alcohol precipitation for 24 h. The supernatant was taken and vacuum dried to obtain a *Hyacinthus orientalis* bulb extract.

In the *Hyacinthus orientalis* bulb extract, the alkaloid content was 3%, the polysaccharide content was 68%, the flavone content was 2%, and the amino acid content was 25%.

In the alkaloids, the 1-DNJ content was 30%.

The total heavy metal content was less than 5 ppm, including 0.08 ppm of lead, 0.01 ppm of mercury, and 0.15 ppm of arsenic, where cadmium was not detected.

Example 16

100 g of fresh *Commelina communi* (*Commelina communi*) leaf was taken and crushed, then added with 500 ml of alcohol water in 2 times, and extracted by heating reflux for 1 h each time. The extracting solutions were combined, and filtered to remove the insoluble matters. The extracting solution was concentrated by heating until the solid content reached 10%, kept at 30° C., and used as a loading solution for the cation resin column.

3.5 g of 732-type strongly acidic styrene-based cation resin was filled in the column. The cation resin was activated according to the method described in Example 3. The concentrated extracting solution was loaded, and then eluted with 800 ml of 2.3 mol/L ammonia water at an elution speed of 10 BV/h. The eluate was collected when the effluent from the cation resin column was detected to be at pH>7. The collection was terminated when the collection solution was up to 300 ml.

The collection solution resulting from the cation resin column separation was filtered via an ultrafiltration membrane to remove purities, and then concentrated through a reverse osmosis membrane. The specific gravity of the concentrated liquid was 1.2. It was transferred to an alcohol precipitation tank, and 5 g of anhydrous ethanol was added when the stirring paddle was at 500 rpm. After adding the ethanol, the solution was stopped stirring, and subjected to alcohol precipitation for 24 h. The supernatant was taken and vacuum dried to obtain a *Commelina* communi leaf extract.

In the *Commelina* communi leaf extract, the alkaloid content was 10%, the polysaccharide content was 27%, the flavone content was 10%, and the amino acid content was 50%.

In the alkaloids, the 1-DNJ content was 50%.

The total heavy metal content was less than 5 ppm, including 0.05 ppm of lead and 0.17 ppm of arsenic, where cadmium and mercury were not detected.

Comparative Example 1

1000 kg of fresh Ramulus Mori (*Morus serrata* Roxb.) of the same batch as that used in Example 3 was taken, and subjected to crude extraction according to the method described in Example 3. The crude extraction solution was concentrated by heating. The specific gravity of the concentrated liquid was 1.1. It was transferred to an alcohol precipitation tank, and 62 kg of anhydrous ethanol was added when the stirring paddle was at 400 rpm. After adding the ethanol, the solution was stopped stirring, and subjected to alcohol precipitation for 24 h. The supernatant was taken and concentrated under reduced pressure to obtain a Ramulus Mori extractum. The alkaloid content was 15%, the polysaccharide content was 40%, the flavone content was 5.2%, and the amino acid content was 30%.

In the alkaloids, the 1-DNJ content was 55%.

The total heavy metal content was 30 to 40 ppm, including 29.11 ppm of lead, 1.50 ppm of cadmium, 0.76 ppm of mercury, and 1.01 ppm of arsenic, in which the content of the lead, cadmium and mercury exceeded the content standards.

Without the cation resin column and anion resin column separation steps, this comparative example exhibited a reduced alkaloid content, a remarkably increased heavy metal content, and a 3-fold increase in amount of ethanol, in comparison to Example 3.

Comparative Example 2

1000 kg of fresh Ramulus Mori (*Morus serrata* Roxb.) of the same batch as that used in Example 3 was weighed, and subjected to crude extraction, concentration by heating, and separation via the cation resin and anion resin according to the method described in Example 3. 870 L of collection solution resulting from the anion resin column separation was transferred to an alcohol precipitation tank, and 135 kg of anhydrous ethanol was added when the stirring paddle was at 400 rpm. After adding the ethanol, the solution was stopped stirring, and subjected to alcohol precipitation for 24 h. The supernatant was taken and concentrated under reduced pressure to obtain a Ramulus Mori extractum. The alkaloid content was 62%, the polysaccharide content was 18%, the flavone content was 1.1%, and the amino acid content was 12%.

In the alkaloids, the 1-DNJ content was 68%.

The total heavy metal content was 10 to 20 ppm, including 10.01 ppm of lead, 0.70 ppm of cadmium, 0.44 ppm of mercury, and 0.83 ppm of arsenic, in which the content of the lead, cadmium and mercury exceeded the content standards.

Without the concentration step between the resin separation and the alcohol precipitation, this comparative example exhibited an increased heavy metal content and a 8-fold increase in amount of ethanol, in comparison to Example 3.

Comparative Example 3

1000 kg of fresh Ramulus Mori (*Morus serrata* Roxb.) of the same batch as that used in Example 3 was weighed, and subjected to crude extraction, concentration by heating, and separation via the cation resin and anion resin according to the method described in Example 3. 870 L of the collection solution resulting from the anion resin column separation was concentrated under reduced pressure to obtain a Ramulus Mori extractum. The alkaloid content was 52%, the polysaccharide content was 22%, the flavone content was 0.8%, and the amino acid content was 20%.

In the alkaloids, the 1-DNJ content was 60%.

The total heavy metal content was 20 to 40 ppm, including 22.15 ppm of lead, 1.45 ppm of cadmium, 0.65 ppm of mercury, and 0.89 ppm of arsenic, in which the content of the lead, cadmium and mercury exceeded the content standards.

Without the alcohol precipitation step after the resin separation, this comparative example exhibited a reduced alkaloid content and a remarkably increased heavy metal content, in comparison to Example 3.

Comparative Example 4

1000 kg of fresh Ramulus Mori (*Morus serrata* Roxb.) of the same batch as that used in Example 3 was taken and crushed, then added with 4-times alcohol water (4000 L), and extracted by heating reflux for 2 h. The extracting solutions were combined, and filtered to remove insoluble matters. The crude extraction solution was concentrated by heating. The specific gravity of the concentrated liquid was 1.1. It was transferred to an alcohol precipitation tank, and 62 kg of anhydrous ethanol was added when the stirring paddle was at 400 rpm. After adding the ethanol, the solution was stopped stirring, and subjected to alcohol precipitation for 24 h. The supernatant was taken and loaded onto the cation resin. According to the method described in Example 3, 150 kg of cation resin was filled in the column, and subjected to cation resin separation and anion resin separation. The collection solution resulting from the anion resin column separation was concentrated under reduced pressure to obtain a Ramulus Mori extractum. The alkaloid content was 51%, the polysaccharide content was 25%, the flavone content was 0.5%, and the amino acid content was 20%.

In the alkaloids, the 1-DNJ content was 55%.

The total heavy metal content was 10 to 20 ppm, including 11.11 ppm of lead, 0.82 ppm of cadmium, 0.50 ppm of mercury, and 0.53 ppm of arsenic, in which the content of the lead, cadmium and mercury exceeded the content standards.

This comparative example carried out the alcohol precipitation prior to the cation resin separation step, and exhibited a reduced alkaloid content, an increased heavy metal content, and a 3-fold increase in amount of ethanol, in comparison to Example 3.

Comparative Example 5

1000 kg of fresh Ramulus Mori (*Morus serrata* Roxb.) of the same batch as that used in Example 3 was taken, and subjected to crude extraction and concentration by heating according to the method described in Example 3. The concentrated crude extraction solution was directly loaded onto the anion resin, and subjected to the anion resin separation according to the method described in Example 3. 3000 L of effluent was collected. The collection solution resulting from the anion resin column separation was centrifuged to remove impurities, and then concentrated via a nanofiltration membrane. The specific gravity of the concentrated liquid was 1.1. It was transferred to an alcohol precipitation tank, and 46 kg of anhydrous ethanol was added when the stirring paddle was at 400 rpm. After adding the ethanol, the solution was stopped stirring, and subjected to alcohol precipitation for 24 h. The supernatant was taken and concentrated under reduced pressure to obtain a Ramulus Mori extractum.

In the Ramulus Mori extractum, the alkaloid content was 40%, the polysaccharide content was 35%, the flavone content was 1.5%, and the amino acid content was 22%.

In the alkaloids, the 1-DNJ content was 50%.

The total heavy metal content was 30 to 40 ppm, including 30.01 ppm of lead, 1.24 ppm of cadmium, 0.21 ppm of mercury, and 0.85 ppm of arsenic, in which the content of the lead, cadmium and mercury exceeded the content standards.

Without the cation resin separation step, this comparative example exhibited a reduced alkaloid content, a remarkably increased heavy metal content, and a 2-fold increase in amount of ethanol, in comparison to Example 3.

Test Example 1 Stability Study

Figure 1:
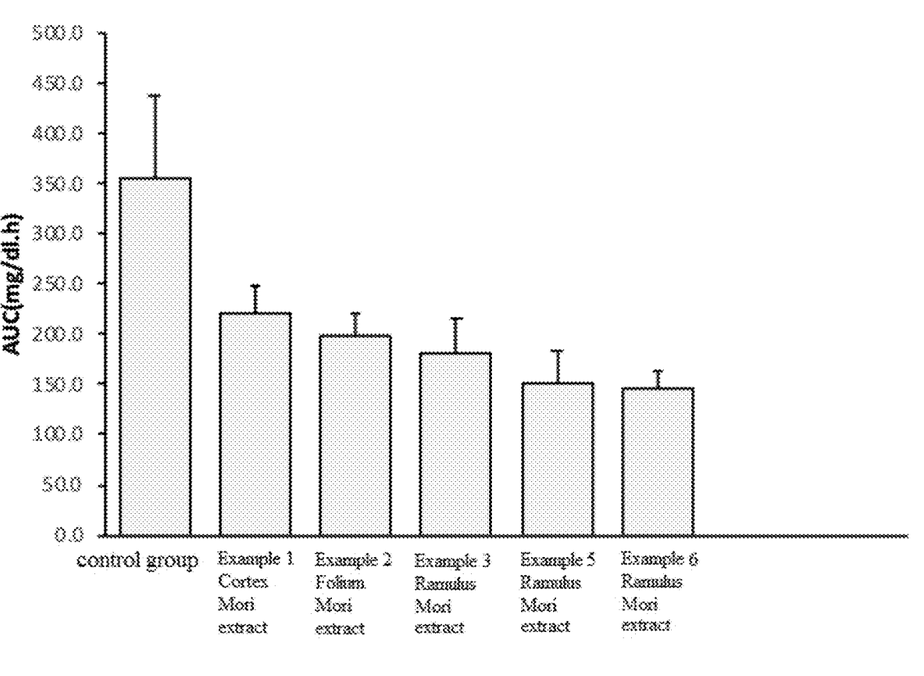
FIG. 1 shows the sucrose tolerance test results of the plant extracts obtained in Examples 1, 2, 3, 5 and 6 in rats.

The Mulberry extract prepared in Example 1, the Folium Mori extracts prepared in Examples 2, 8, and 9, the Ramulus Mori extracts prepared in Examples 3 and 5-7, and the Cortex Mori extracts prepared in Examples 4 and 10 were sealed and packaged in composite film bags, then left for 24 months at a temperature of 25° C.±2° C. and a relative humidity of RH60%±10%, and thereafter the content of alkaloids therein was tested. The results were listed in Table 1 below.

overnight before test. One of the groups was orally administered with sucrose solutions (4.0 g/kg) as a control group (Normal), while the remaining 5 groups were orally administered with sucrose as well as the Cortex Mori extract sample prepared in Example 1, the Folium Mori extract sample prepared in Example 2, and the Ramulus Mori extract samples prepared in Examples 3, 5, and 6 (10 mg/kg for each in terms of the total alkaloids) as administration groups. The blood glucose levels prior to the administration (0 min) and at 30 min, 60 min, and 120 min after administration were measured. The time-blood glucose curve was plotted, and the area under curve (AUC) of blood glucose was calculated. The results were as shown in FIG. 1.

The results indicate that the plant extracts obtained by the plant extraction method of the present disclosure result in a significant decrease in the elevation of blood glucose in normal mice after sucrose loading.

The present disclosure was explained above with reference to the preferred embodiments, which are, however, only exemplary and illustrative. On this basis, various substitutions and improvements can be made to the present disclosure, and all of them fall within the scope of protection for the present disclosure.

What is claimed is:

1. A plant extraction method comprising the following steps of:
    step 1): preparing a crude plant extraction solution by using a plant raw material; and concentrating the crude plant extraction solution;
    step 2): separating the concentrated crude extraction solution via a cation resin and an anion resin to obtain a collection solution; wherein:
        the cation resin is one or a combination of more selected from a strongly acidic cation exchange resin, a weakly acidic cation exchange resin, and a strongly alkaline quaternary ammonium-type cation resin;

TABLE 1

| | Content/% | | | | | | | | | |
|---|---|---|---|---|---|---|---|---|---|---|
| Items | Example 1 Mulberry Extract | Example 2 Folium Mori Extract | Example 3 Ramulus Mori Extract | Example 4 Cortex Mori Extract | Example 5 Ramulus Mori Extract | Example 6 Ramulus Mori Extract | Example 7 Ramulus Mori Extract | Example 8 Folium Mori Extract | Example 9 Folium Mori Extract | Example 10 Cortex Mori Extract |
| Total alkaloids | 44.8 | 59.5 | 74.3 | 57.2 | 97.2 | 96.7 | 14.8 | 4.9 | 2.9 | 2.9 |
| 1-DNJ | 59.4 | 68.8 | 71.3 | 66.9 | 98.1 | 97.5 | 54.9 | 45.7 | 37.7 | 42.8 |

It is clear from Table 1 that the plant extracts obtained by the extraction method of the present disclosure have good stability.

Test Example 2 Residual Organic Solvents

The gas chromatography was used to detect the residual resin, including n-hexane, methyl cyclohexane, divinylbenzene, toluene, benzene, xylene, and styrene. The plant extracts prepared in Examples 1 to 9 were tested, and none of them was detected to contain residual resin.

Test Example 3 Efficacy Test

Normal male ICR mice were randomly divided into 6 groups (n=10) depending upon body weight, and fasted the amount of the cation resin used and the plant raw material have a weight ratio ranging from 1:1 to 1:30;

an eluent for the cation resin is a salt solution containing cations or an alkaline solution containing cations; and the cations in the eluent have a concentration ranging from 0.04 to 5 mol/L;

collection from the cation resin begins when the pH of the effluent is higher than 7 or the starting point of the collection of the effluent is determined according to properties of components to be separated as determined by utilizing a precipitation reaction; and the collection from the cation resin is terminated when the volume of the collection solution reaches 0.1 to 10 times the weight of the plant raw material;

a weight of the eluent used for the separation via the cation resin is 0.1 to 30 times the weight of the plant raw material;

the anion resin is one or a combination of more selected from a strongly alkaline anion exchange resin, a weakly alkaline anion exchange resin, and a weakly acidic anion exchange resin; and the amount of the anion resin used and the plant raw material have a weight ratio ranging from 1:1 to 1:80;

collection from the anion resin is terminated when the volume of the collection solution reaches 0.05 to 10 times the weight of the plant raw material;

step 3): concentrating the collection solution obtained in step 2);

step 4): subjecting the concentrated solution obtained in step 3) to alcohol precipitation using ethanol as the alcohol, wherein the ethanol used for the alcohol precipitation and the plant raw material have a weight ratio ranging from 1:4 to 1:600; and optionally, step 5): concentrating and drying, wherein the plant is a branch of a plant of the genus *Morus*;

a plant extract obtained by the plant extraction method contains each component in the following weight ratios with respect to a total weight of the plant extract: alkaloids 30% to 99%; polysaccharides 0.2% to 35%; flavones 0.05% to 2%; amino acids 0% to 25%; and other components 0% to 20%;

the alkaloids in the plant extract contain 1-deoxynojirimycin with a weight content of 50% to 99% with respect to a total weight of the alkaloids, and the heavy metal content of the plant extract is not more than 10 ppm.

2. The extraction method according to claim 1, wherein the plant is any one or a combination of more selected from *Morus multicaulis* Perrott., *Morus alba* L., *Morus atropurpurea* Roxb., *Morus* mizuho Hotta., *Morus* wittiorum Hand Mazz., *Morus laevigata* Wall., *Morus nigra* Linn., *Morus cathayana* Hemsi., *Morus serrata* Roxb., *Morus mongolica* Schneid., *Morus bombycis* Koidz., *Morus notabilis* Schneid., *Morus* nigriformis Koidz., *Morus yunnanensis* Koidz., *Morus australis* Poir., *Morus mongolica* (Bur.) Schneid var. diabolica Koidz., *Morus alba* L. var. macrophylla loud, *Morus alba* Var. *Pendula* Dippel, and *Morus alba* L. var. venosa Delili.

3. The extraction method according to claim 2, wherein the plant is *Morus atropurpurea* Roxb, *Morus multicaulis* Perrott., *Morus alba* L., *Morus serrata* Roxb., or *Morus bombycis* Koidz.

4. The extraction method according to claim 1, wherein the plant is Yuesang No. 11, Guisangyou No. 62 or Sangteyou No. 2.

5. The extraction method according to claim 1, wherein the cation resin is one or a combination of more selected from 732-type strongly acidic styrene-based cation exchange resin, 734-type strongly acidic styrene-based cation exchange resin, 002SC-type strongly acidic styrene-based cation exchange resin, D001-type macroporous and strongly acidic styrene-based cation exchange resin, D113-type macroporous and weakly acidic cation exchange resin, and D254-type macroporous and strongly alkaline quaternary ammonium-type cation exchange resin.

6. The extraction method according to claim 1, wherein the cation resin is 732-type strongly acidic styrene-based cation exchange resin, 734-type strongly acidic styrene-based cation exchange resin and D001-type macroporous and strongly acidic styrene-based cation exchange resin.

7. The extraction method according to claim 1, wherein upon separation via the cation resin in step 2), the cation resin and the plant raw material have a weight ratio ranging from 1:1 to 1:25.

8. The extraction method according to claim 7, wherein upon separation via the cation resin in step 2), the cation resin and the plant raw material have a weight ratio ranging from 1:2 to 1:20.

9. The extraction method according to claim 1, wherein the weight of the eluent used for the separation via the cation resin in step 2) is 0.5 to 10 times the weight of the plant raw material.

10. The extraction method according to claim 1, wherein the anion resin is one or a combination of more selected from 717-type strongly alkaline styrene-based anion exchange resin, 711-type strongly alkaline styrene-based anion exchange resin, D201-type macroporous and strongly alkaline styrene-based anion exchange resin, D218-type macroporous and strongly alkaline acrylic-based anion exchange resin, D301-G-type macroporous and weakly acidic styrene-based anion exchange resin, and D301-type macroporous and weakly alkaline styrene-based anion exchange resin.

11. The extraction method according to claim 10, wherein the anion resin is 717-type strongly alkaline styrene-based anion exchange resin, D201-type macroporous and strongly alkaline styrene-based anion exchange resin, and D218-type macroporous and strongly alkaline acrylic-based anion exchange resin.

12. The extraction method according to claim 1, wherein upon separation via the anion resin in step 2), the anion resin and the plant raw material have a weight ratio ranging from 1:1 to 1:64.

13. The extraction method according to claim 12, wherein upon separation via the anion resin in step 2), the anion resin and the plant raw material have a weight ratio ranging from 1:1 to 1:32.

14. The extraction method according to claim 1, wherein ethanol used for the alcohol precipitation in step 4) and the plant raw material have a weight ratio ranging from 1:20 to 1:300.

15. A plant extraction method comprising the following steps of:

step 1): preparing a crude plant extraction solution by using a plant raw material; and concentrating the crude plant extraction solution;

step 2): separating the concentrated crude extraction solution via a cation resin and an anion resin to obtain a collection solution; wherein:

the cation resin is one or a combination of more selected from a strongly acidic cation exchange resin, a weakly acidic cation exchange resin, and a strongly alkaline quaternary ammonium-type cation resin;

the amount of the cation resin used and the plant raw material have a weight ratio ranging from 1:1 to 1:30;

an eluent for the cation resin is a salt solution containing cations or an alkaline solution containing cations; and the cations in the eluent have a concentration ranging from 0.04 to 5 mol/L;

collection from the cation resin begins when the pH of the effluent is higher than 7 or the starting point of the collection of the effluent is determined according to properties of components to be separated as determined by utilizing a precipitation reaction; and the collection from the cation resin is terminated when the volume of the collection solution reaches 0.1 to 10 times the weight of the plant raw material;

a weight of the eluent used for the separation via the cation resin is 0.1 to 30 times the weight of the plant raw material;

the anion resin is one or a combination of more selected from a strongly alkaline anion exchange resin, a weakly alkaline anion exchange resin, and a weakly acidic anion exchange resin; and the amount of the anion resin used and the plant raw material have a weight ratio ranging from 1:1 to 1:80;

collection from the anion resin is terminated when the volume of the collection solution reaches 0.05 to 10 times the weight of the plant raw material;

step 3): concentrating the collection solution obtained in step 2);

step 4): subjecting the concentrated solution obtained in step 3) to alcohol precipitation using ethanol as the alcohol, wherein the ethanol used for the alcohol precipitation and the plant raw material have a weight ratio ranging from 1:4 to 1:600; and optionally, step 5): concentrating and drying, wherein the plant is a branch of a plant selected from the group consisting of *Hyacinthus orientalis, Adenophora Triphylla* var. *japonica*, and *Commelina* communis;

a plant extract obtained by the plant extraction method contains each component in the following weight ratios with respect to a total weight of the plant extract: alkaloids 30% to 99%; polysaccharides 0.2% to 35%; flavones 0.05% to 2%; amino acids 0% to 25%; and other components 0% to 20%;

the alkaloids in the plant extract contain 1-deoxynojirimycin with a weight content of 50% to 99% with respect to a total weight of the alkaloids, and the heavy metal content of the plant extract is not more than 10 ppm.

* * * * *